United States Patent [19]

Belanger et al.

[11] Patent Number: 5,443,981
[45] Date of Patent: Aug. 22, 1995

[54] ACREMONIUM TYPHINUM ATCC 74228 WHICH EXHIBITS ENDOPROTEOLYTIC ACTIVITY

[75] Inventors: Faith C. Belanger, East Brunswick; Jon T. Lindstrom, South River, both of N.J.

[73] Assignee: Rutgers, the State University, New Brunswick, N.J.

[21] Appl. No.: 217,489

[22] Filed: Mar. 24, 1994

Related U.S. Application Data

[63] Continuation-in-part of Ser. No. 74,137, Jun. 9, 1993, abandoned.

[51] Int. Cl.$^6$ ............... C12N 9/58; C12N 1/00; C12N 1/14; A01N 63/00
[52] U.S. Cl. ................... 435/223; 435/911; 435/254.1; 435/814; 435/820; 424/93.5; 424/94.63
[58] Field of Search ............ 435/219, 911, 254.1, 435/223, 814, 820; 252/174.12, DIG. 12; 424/93.5, 94.63

[56] References Cited

PUBLICATIONS

Lindstrom et al., Supplement to *Plant Physiology*, vol. 102, No. 1, May 1993, p. 113.
Lindstrom et al., *Plant Physiol.*, vol. 102, pp. 645–650, 1993.
Lindstrom et al., Supplement to *Plant Physiology*, vol. 99, No. 1, 1992, p. 111.

*Primary Examiner*—David M. Naff
*Assistant Examiner*—Michael Meller
*Attorney, Agent, or Firm*—Omri M. Behr; Matthew J. McDonald

[57] ABSTRACT

A crude membrane fraction of leaf sheath tissue of a grass endophytically infected by *A. typhinum* is produced. The extract exhibits endoproteolytic activity in the presence of detergent or after methanol precipitation. This activity is optimal at 35°–40° C. and pH 10–11 and is exhibited only when a reductant is present. The activity is associated with a first gel electrophoresis band having apparent molecular weight of 205,000 daltons when said extract is electrophoresed without prior boiling; however, when said extract is boiled prior to electrophoresis, there results a band having apparent molecular weight of 34,000 daltons. This band gives rise to polyclonal rabbit antibodies which are not cross react with proteinase K. The preferred source of *Acremonium typhinum* is ATCC 74228.

12 Claims, 8 Drawing Sheets

| ACTIVITY, % | 78 | 100 | 57 | 9 | 2 | 0 |
|---|---|---|---|---|---|---|
| TEMPERATURE, C | 27 | 37 | 42 | 55 | 65 | 100 |

ACREMONIUM TYPHINUM ATCC 74228 WHICH EXHIBITS ENDOPROTEOLYTIC ACTIVITY

This is a continuation-in-part of U.S. patent application Ser. No. 08/074,137 filed Jun. 9, 1993 by Belanger et al, abandoned.

FIELD OF THE INVENTION

A endoproteolytic proteinase expressed by the fungus *Acremonium typhinum*, particularly during endophytic infection of grass species of the Poa genus.

BACKGROUND OF THE INVENTION

Endophytic fungel infection of grasses has been recognized for nearly one hundred years. An "endophyte" is defined as "an organism that lives its life cycle within a host plant without causing disease". Fungal endophytes exist exclusively in the intercellular spaces of the plants, primarily in sink tissues of the plant, such as leaf sheaths and pith. The endophytes do not invade the plant cells and their presence is often completely asymptomatic.

Fungal endophytes infect many wild and cultivated grass species and these associations have major ecological and agricultural impacts. Many of the endophytic fungi which infect commercially important forage and turfgrasses belong to the genus Epichloe and its asexual anamorphs which have been classified as Acrernonium section Albo-lanosa. Clay, *Ecology*, 69, No. 1, 10-16 (1988). In the case of the asexual Acrernonium spp., infection of the host causes no symptoms. One grass which is endophytically infected by *Acrernonium typhinum* is the highly apomictic big blue grass (*P. ampla*) cultivar Service (PI387931), released by the Alaska Department of Natural Resources as an improved grass for roadside vegetation.

In many instances, the endophyte-grass association is strictly symbiotic, with the fungus conferring benefits on the plant. One of these benefits is reduced herbivory by insects and animals due to the production of toxic alkaloids. A major drawback of endophyte infection however is that toxic alkaloids in endophyte-infected forage grasses can cause grazing livestock to be poisoned.

The insect deterrence conferred by Acremonium endophyte infection imparts considerable advantage to forage and turfgrass. Therefore, turfgrass breeders wish to improve grasses through use of new combinations of endophytes and grasses. It is known, however, that there is limited compatibility between various endophyte isolates and grasses other than their natural hosts; most attempts to produce novel endophyte-host relationships have failed. This seems to be due to the fact that the specific interactions between the fungal endophytes and their host grasses which result in effective infection are completely unknown.

SUMMARY

There is provided a crude membrane fraction of *A. typhinum* exhibiting endoproteolytic activity. This fraction is reactive with BCA. The proteolytic activity is optimal at 35°-40° C. and at pH 10-11, and is exhibited only when a reductant (such as, for example, β-mercaptoethanol or DTT) is present. The endoproteolytic activity however is inhibited by the protease inhibitor PMSF, but not by protease inhibitors EDTA, EGTA, phenanthroline, E-64 and DCI. Moreover, the proteolytic activity is not inhibited by the presence of detergent or by methanol precipitation. This activity is associated with a first gel electrophoresis band having apparent molecular weight of 205,000 daltons when said extract is electrophoresed without prior boiling; however, when said extract is boiled prior to electrophoresis, a band having apparent molecular weight of 34,000 daltons is instead produced. This 34,000 dalton band comprises a thiol group, reacts with biotinylated lectins selected from the group consisting of *P. sativum* agglutinin, wheat germ agglutinin, and peanut agglutinin, and gives rise to polyclonal rabbit antibodies which do not cross react with proteinase K, a secreted enzyme produced by the saprophytic fungus *Tritirachium album* Limber.

There are further provided a cell wall and intracellular extract of *A. typhinum*, said extract being reactive with BCA and exhibiting the endoproteolytic activity of the crude membrane fraction described above. Either the cell wall or the intracellular extract may be isolated from leaf sheath tissue of a grass endophytically infected by *A. typhinum* ATCC 74228. Suitable grasses include a grass selected from the group consisting of *P. ample, P. arctica, P. autumnalis, P. interior, P. palustris,* and *P. sylvestris*. In any of these cell wall or the intracellular extracts, the endophytic infection may suitably be a culture of *A. typhinum* ATCC 74228 selected from the group consisting of a primary culture of said fungus and a sub-culture thereof 7-14 days after subculturing.

There is further provided a proteinase which is derivable from any of the crude membrane, cell wall or intracellular extracts described above. This protease acts on natural polypeptides and should be therefore be termed a proteinase. The proteinase is reactive with BCA and exhibits endoproteolytic activity. This activity is optimal at 35°-40° C. and at pH 10-11, and is exhibited only when a reductant (such as, for example, β-mercaptoethanol or DTT) is present. The proteolytic activity is inhibited by the protease inhibitor PMSF, but not by the protease inhibitors EDTA, EGTA, phenanthroline, E-64 and DCI or by the presence of detergent or by methanol precipitation. This activity is associated with a first gel electrophoresis band having apparent molecular weight of 205,000 daltons when said proteinase is electrophoresed without prior boiling; however, when said proteinase is boiled prior to electrophoresis, a band having apparent molecular weight of 34,000 daltons is instead produced. This 34,000 dalton band comprises a thiol group, reacts with biotinylated lectins selected from the group consisting of *P. sativum* agglutinin, wheat germ agglutinin, and peanut agglutinin, and gives rise to polyclonal rabbit antibodies which do not cross react with proteinase K.

This proteinase is the first proteinase isolated from *A. typhinum*, and accordingly is hereinafter referred to as "proteinase At1". The substantially pure form of the proteinase is a non-naturally occurring composition of matter; it may only be made by performance of the purification steps described below. The purified proteinase has a distinctive character, as a detergent-stable proteinase, and distinctive uses, described below in connection with the detergent compositions.

Still further, there is provided a proteinase isolated from a crude membrane fraction of an endophytically infected grass selected from the group consisting of *P. arcfica* R. Br., *P. autumnalis* Muhl. ex Ell., *P. interior* Rydb., *P. palustris* L., and *P. sylvestris* A. Gray. This proteinase also is reactive with BCA and exhibits endoproteolytic activity. This activity is exhibited only when a reductant (such as, for example, β-mercaptoethanol or DTT) is present and is uninhibited by the presence of detergent or by methanol precipitation. The endoproteolytic is associated with a first gel electrophoresis band having apparent molecular weight of 205,000 daltons when said proteinase is electrophoresed without prior boiling; however, when the proteinase is boiled prior to electrophoresis, a band having apparent molecular weight of 34,000 daltons is instead produced. This 34,000 dalton band is immunologically cross-reactive with the polyclonal rabbit antibodies specific to said proteinase described above. This proteinase is equally a non-naturally occurring composition of matter and shares the distinctive character and use of proteinase At1.

The binding of the 34,000 dalton band from the proteinase which is derivable from any of the crude membrane, cell wall or intracellular extracts described above with the named biotinylated lectins indicates the proteinase include α-linked mannose and α-linked glucose, N-acetyl glucosamine, and galactosyl end-groups, thus making the proteinase a glycoprotein. Furthermore, a purified sample of this proteinase becomes fluorescent upon exposure to fluorescein-5-maleimide (F5M) or 5-iodoacetamidofluorescein (IAF), indicating the presence of at least one thiol group in the proteinase.

Yet another embodiment provides a composition comprising one of the proteinases described above and one or more detergents.

Figure 1:
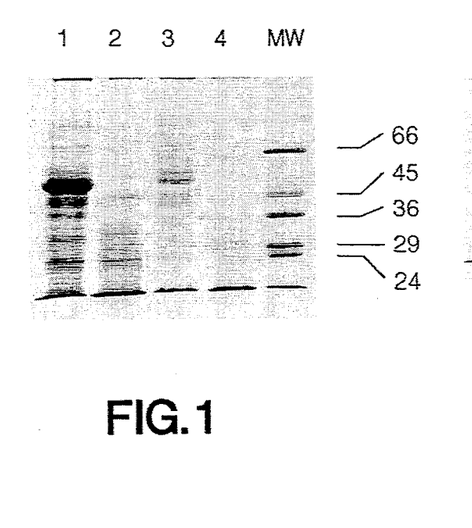

A further embodiment of the invention is a biologically pure culture of the microorganism *A. typhinum* having the identifying characteristics of *A. typhinum*, and being capable of producing the proteinase At1 in recoverable amounts. Included among such embodiments is a biologically pure culture of *A. typhinum* ATCC 74228 which produces recoverable amounts of the proteinase At1. This biologically pure culture is believed to be a non-naturally occurring composition of matter, resulting only by the performance of the purification steps described below. As a result of performing these steps, the pure culture has as a distinctive character the ability to synthesize proteinase At1 with a minimum of non-fungal by-products.

Yet another embodiment of the invention is a process of synthesizing the proteinase At1 comprising cultivating *A. typhinum* ATCC 74228 under conditions suitable for the formation of said proteinase and recovering said proteinase in substantially pure form; and the proteinase made by this process.

BRIEF DESCRIPTION OF THE FIGURES

FIG. 1. SDS-PAGE analysis of total protein extracts from endophyte-free and endophyte-infected *Poe ample* leaf blades and leaf sheaths.

FIG. 2. SDS-PAGE analysis of BSA with endophyte-infected *Poe ample* leaf sheath extract.

FIG. 3. SDS-PAGE analysis of BSA with *Acremonium typhinum* extract.

FIG. 4. SDS-PAGE analysis of endophyte-infected leaf sheath extract and BSA in the presence of a reductant or of inhibitors PMSF and E-64.

FIG. 5. SDS-PAGE analysis of protease activity of crude membrane and supernatant fractions.

FIG. 6. Visualization of the protease activity in an SDS-gelatin gel.

FIG. 7. SDS-PAGE analysis of protease activity in extracts from other endophyte-infected grasses.

FIG. 8. SDS-gelatin activity analysis of intracellular and cell wall extracts of *P. ampla* leaf sheath tissue.

FIG. 9. SDS-PAGE analysis of the intracellular and cell wall localized proteinase At1.

FIG. 10. SDS-PAGE analysis of denatured cell wall localized proteinase At1.

FIG. 11. SDS-PAGE analysis of cell wall localized proteinase At1 labeled by fluorescein-5-maleimide (F5M) or 5-iodoacet-amidofluorescein (IAF).

FIG. 12. Graphs demonstrating the effect of pH on cell wall localized proteinase At1 activity.

Part A: Graph of proteinase At1 activity with azoalbumin as substrate

Part B: Graph of proteinase activity with succinyl-Ala-Ala-Pro-Phe-4-nitroanilide as substrate.

FIG. 13. SDS-PAGE analysis of cell wall localized proteinase At1 after incubation different temperatures.

FIG. 14. SDS-PAGE analysis of cell wall localized proteinase At1 exposed to various biotinylated lectins.

FIG. 15. SDS-PAGE and immunoblot analysis (using cell wall localized proteinase At1 affinity purified antiserum) to measure expression of proteinase At1 in culture.

FIG. 16. Analysis of leaf sheath crude membrane fractions from other Poa species.

Part A: Immunoblot analysis using proteinase At1 antiserum

Part B: SDS-gelatin activity gel analysis

DETAILED DESCRIPTION OF THE PREFERRED EMBODIMENTS

The following abbreviations are used herein:

| | |
|---|---|
| At1 | the proteinase having the characteristics specified above and isolated from *A. typhinum* ATCC 74228 |
| BCA | bicinchoninic acid |
| BCIP | 5-bromo-4-chloro-3-indolyl phosphate |
| Bis-Tris | bis-(2-hydroxyethyl)imino-tris(hydroxymethyl) methane |
| Bis-Tris propane | 1,3-bis[tris(hydroxymethyl)methylamino] propane |
| BSA | bovine serum albumin |
| CAPS | cyclohexylamino-1-propanesulfonic acid |
| CAPSO | 3-(cyclohexylamino)-2-hydroxy-1-propanesulfonic acid |
| DCI | 3,4-dichloroisocoumarin |
| DFP | diisopropylfluorophosphate |
| E-64 | L-trans-epoxysuccinyl-leucylamido (4-guanidino) butane |
| F5M | fluorescein-5-maleimide |
| IAF | 5-iodoacetamidofluorescein |
| MS | Murashige and Skoog basal medium |
| NBT | nitroblue tetrazolium |
| PDA | potato dextrose agar |
| PMSF | phenylmethylsulfonyl fluoride |
| PAGE | polyacrylamide gel electrophoresis |
| SDS | sodium dodecyl sulfate |
| Tris | tris(hydroxymethyl)aminomethane |

A. THE CRUDE MEMBRANE FRACTION

In working with fractions extracted from a grass endophytically infected by *Acrernonium typhinum*, it was noted that increased protease activity results from the presence of the detergent SDS in buffer. To test whether this detergent might assist in extracting a membrane-bound protease, the protease activity of a crude membrane fraction from the endophytically infected grass is isolated and evaluated.

One skilled in the art would expect the gels from an infected grass to have approximately the same number of protein bands or more than gels from the uninfected grass, due to contribution of the endophyte's proteins. As seen in FIG. 1 however, the fractions from the endophytically infected grass are found to have a surprisingly simpler pattern than the uninfected grass. Two separate crude membrane fractions made from the leaf blade and leaf sheath respectively of the highly apomictic big blue grass (*P. ampla*) cultivar Service (PI387931), released by the Alaska Department of Natural Resources with an endophytic *A. typhinum* infection are subjected to SDS gel electrophoresis. Two separate extracts are made from the leaf blade and sheath of uninfected *P. ample* as controls.

The crude fractions are made as follows. Plant tissue or isolated fungal mycelia are homogenized with sand in 2×SDS sample buffer in a ratio of 0.1 g/400 ml. The extracts are centrifuged to remove debris. The crude fractions are found to be reactive with BCA.

Electrophoretic Patterns of the Crude Membrane Fraction. Aliquots of the supernatant are subjected to SDS-polyacrylamide gel electro-phoresis (SDS-PAGE). 2×SDS buffer is 125 mM tris[hydroxymethyl]-aminomethane (Tris) (pH 6.8), 4.6% (w/v) sodium dodecyl sulfate (SDS), 10% (v/v) $\beta$-mercaptoethanol, 20% (v/v) glycerol, and 0.002% bromophenol blue. SDS-PAGE is carried out using 10% polyacrylamide gels which are stained with coomassie brilliant blue. The gels from the infected leaf blade (lane 2) have far fewer bands at high molecular weight than the uninfected blade (lane 1), and the infected sheath gel is nearly free of protein bands (lane 4), while the uninfected sheath (lane 3) has about as many bands as the uninfected blade.

This disparity indicates a proteolytic activity which is active even in the presence of the strong detergent SDS. The detergent-stability is evaluated by testing the ability of the above extracts to degrade an exogenous protein, bovine serum albumin ("BSA").

Protease inhibition assays described herein employ leaf sheaths from endophyte infected *P. ampla* and mycelium from the isolated endophyte ground in a buffer consisting of 125 mM Tris, pH 8.0 and 4.6% (w/v) SDS. Samples are centrifuged 10 min in a microcentrifuge and the supernatant is removed to a new tube. Protein concentration in the supernatant is determined using the BCA protein assay from Pierce Chemical Company (described in the Pierce product Instructions, incorporated herein by reference). For each comparison, approximately 17.5 $\mu$g of protein from *P. ampla* are used and 7.5 mg protein from the endophyte. More *P. ampla* protein is used since the majority of proteins in these samples are of plant origin.

Figure 2:
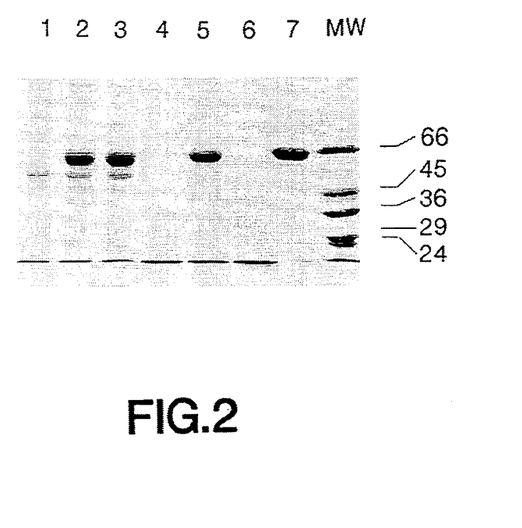

As can be seen in FIG. 2, lane 6, incubation of BSA with the crude membrane fraction from the endophyte-infected tissue results in extensive degradation of BSA. The observed degradation of BSA is considered to be enzymatic because boiling the extract prior to incubation with BSA results in no detectable degradation (FIG. 2, lane 5). Discrete bands of BSA fragments are produced by the protease (FIG. 2, lane 6), indicating that it is an endoprotease. Although endophyte-free plants are expected to contain multiple proteases, the assay found no detectable degradation of BSA (FIG. 2, lane 3). These results indicate that one or more proteases which maintain their activity in 2×SDS buffer are present in the endophyte-infected plant extract but not in the endophyte-free extract.

Mycelial Extract. Proteolytic activity resembling that observed in the crude membrane fraction from endophytically-infected plants is found in an extract of the fungal mycelium isolated from infected *P. ampla* plants.

*A. typhinum* cultures growing on PDA plates are the source of fungal tissue which exhibit proteolytic activity. The endophytic fungus is isolated by surface sterilizing small pieces of leaf sheath tissue for 15 minutes in 1.25% sodium hypochlorite, then rinsing the tissue in sterile water, and placing it on PDA plates. The isolated *A. typhinum* endophyte is cultured in vitro on potato dextrose agar (PDA) (Difco, Detroit, Mich.) plates. After 2–3 weeks in the dark at 24° C., fungal mycelia began to emerge.

Crude fungal membrane preparations are obtained by grinding mycelia of the fungal culture in 125 mM Tris-HCl (pH 8.0). The sample is filtered through Miracloth (22–25 microns) (Calbiochem Corporation, La Jolla, Calif.) and centrifuged at 3,000×g for 10 min to remove unbroken cells and cell walls. An aliquot of the supernatant is reserved and the remainder brought to 11.5 mls with additional buffer and centrifuged at 100,000×g for 60 min to pellet membranes. The membrane pellet obtained is solubilized in 200 ml of 125 mM Tris-HCl, pH 8.0 with 4.6% SDS. The resuspended pellet is centrifuged 10 min in a microcentrifuge (13,000×g) and the supernatant saved as the crude membrane fraction. Protein concentrations in the fractions are determined using the BCA assay. Protease activity in the samples is monitored by assaying BSA degradation. Five $\mu$g of protein are used from each fraction. The protease is activated by adding $\beta$-mercaptoethanol to 10% and allowing the samples to incubate 30 min at room temperature. Five $\mu$g of BSA are added to each sample and digestion proceeded for 30 additional minutes.

Figure 3:
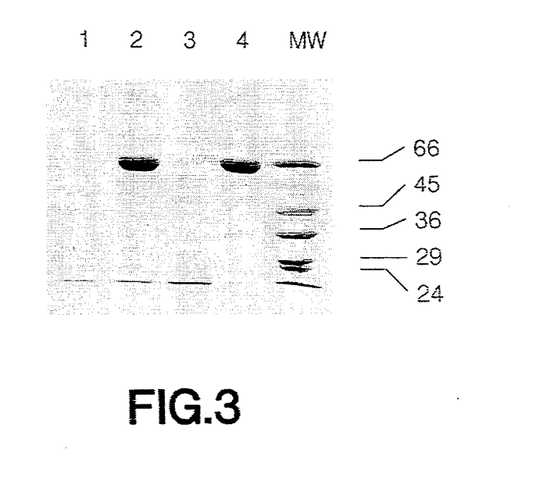

The fungal extract, in 2×X SDS buffer, is found to degrade BSA (FIG. 3, lane 3). These results indicate that the novel protease activity observed in the grass-endophyte interaction is from the fungus.

Figure 5:
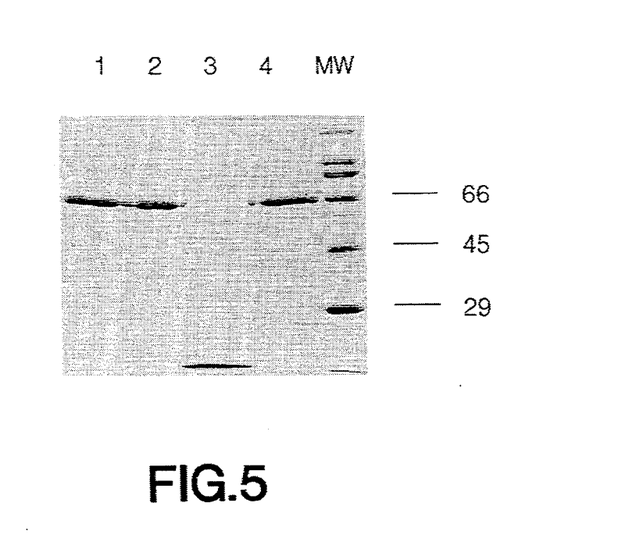

Soluble and a crude membrane fractions are prepared from fungal mycelia as above and assayed for their ability to degrade BSA as above. There is no detectable activity in the 100,000×g supernatant (FIG. 5, lane 2) whereas the BSA is completely degraded by the crude membrane fraction (FIG. 5, lane 3). This data indicate that the fungal protease is associated with membranes.

Detection of enzyme activity following protein electrophoresis can be used to estimate the molecular mass of the active form of the proteinase exhibiting the proteolytic activity. Activity gels are often run with native gels to avoid denaturation of the enzyme by SDS. However, here SDS-PAGE gels are used because the fungal protease is active even in the presence of 4.6% SDS.

The gels are 4% (w/v) polyacrylamide with 0.3% (w/v) gelatin co-polymerized into the matrix. Gels are run 16 h at 4° C. with a current of 6 mA. Immediately after the run, gels are soaked in an activity buffer of 125 mM Tris, pH 8.0 and 2.5% $\beta$-mercaptoethanol for six hours at 37° C. Because SDS does not inhibit the activity of this protease, the conventional step of incubation in Triton X-100 to allow renaturation of proteases is eliminated. Gels are stained with coomassie brilliant blue and destained. Areas of protease activity appear as clear bands against the blue background.

Figure 6:
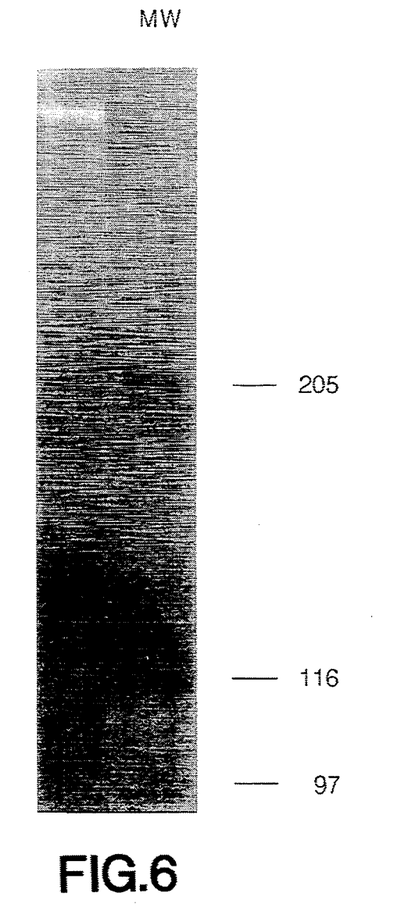

The activity from a mycelial crude membrane fraction is shown in FIG. 6. Because of the high apparent molecular mass of the active protease, 4% gels are used. A single band of activity is detected at a position considerably higher than the highest protein marker of 205,000 daltons.

Need for Reductant and Effect of Protease Inhibitors. To categorize the type of protease activity, the crude membrane fraction from endophytically infected plants is tested in the presence of compounds known to inhibit certain types of proteases. Thus, the fraction is tested with PMSF, an inhibitor of serine and thiol proteases, and with E-64, a specific thiol proteinase inhibitor. The fractions tested with these inhibitors are taken from leaf sheath and fungal mycelia, prepared as described above.

Figure 4:
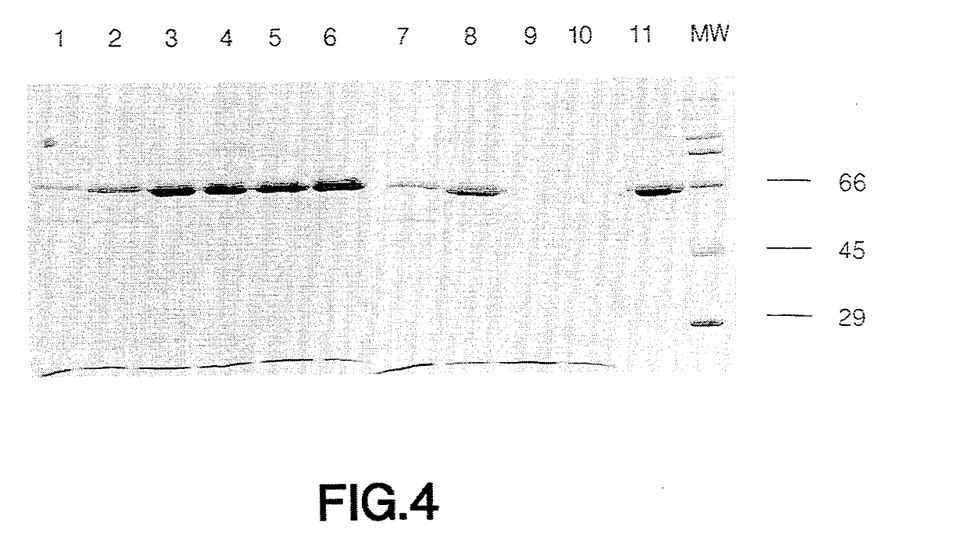

Proteolytic activity present in control fractions from both *P. ampla* and *A. typhinum* (FIG. 4, lanes 1 and 2) have an identical pattern of BSA degradation, confirming that the protease activity in the endophyte-infected plants is of fungal origin. In both cases, the addition of PMSF inhibits BSA degradation (FIG. 4 lanes 3 and 4) whereas E-64 has no detectable effect on protease activity (FIG. 4, lanes 7 and 8). Omission of the reductant β-mercaptoethanol inhibits all detectable proteolytic activity in both plant and fungal samples (FIG. 4, lanes 5 and 6). Dithiothreitol could be substituted for β-mercaptoethanol (data not shown). From these results, it appears that the fungal protease in the crude membrane fraction is a serine protease which requires a reducing agent for activity.

Figure 11:
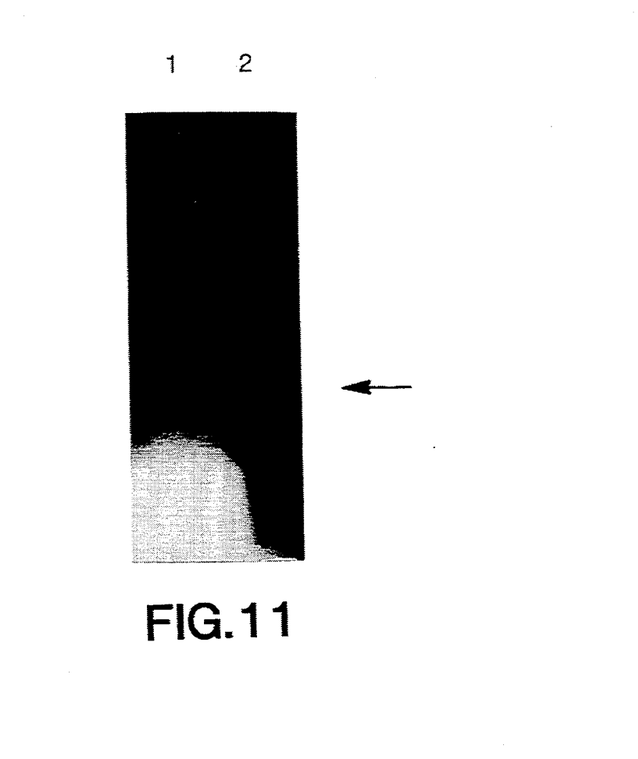

Presence of a Thiol Group. The requirement for a reductant for proteinase At1 activity indicates a thiol group essential for activity might be present in the proteinase. To test this possibility, the purified intracellular proteinase At1 is labeled with F5M, which reacts exclusively with free thiol groups (FIG. 11, lane 2), and with 5-1AF, a reagent which preferentially reacts with free thiol groups, although it can also react with other groups (FIG. 11, lane 1). Identical results are obtained with 5-1AF as with F5M. These results confirm the presence of at least one thiol group in proteinase At1.

The optimal pH and temperature of the crude membrane fraction's endoproteolytic activity and the reactivity with certain lectins are discussed below.

B. THE CELL WALL AND INTRACELLULAR EXTRACTS

The crude membrane fraction may be further purified beyond the crude fraction level, and localized to both the cell wall and intracellular positions. The cell wall and intracellular extracts are found to share the proteolytic activity of the crude membrane fraction.

Intracellular Extract exhibiting proteolytic activity. An intracellular extract is isolated as follows. 2.5 g of *P. ampla* leaf sheath tissue is homogenized with sand, in a 10-fold (w/v) volume of 100 mM Tris, pH 8.0. The homogenate is filtered through Miracloth (22–25 mm) (Calbiochem, La Jolla, Calif.) and centrifuged at 3,000 g for 10 min to pellet the cell walls. The supernatant is centrifuged at 100,000 g for 60 min at 4° C. to pellet membranes. The membrane pellet is resuspended in 800 ml of 100 mM Tris, pH 8.0 and transferred to a microfuge tube. The solution is made to 20 mM DTT and incubated at 37° C. for 10 min. This step results in solubilization of a significant fraction of the proteinase activity. The resuspended pellets are again centrifuged 100,000 g for 60 min. The second 100,000 g supernatant, which generally contains over 40% of the proteinase activity, is concentrated using first a Centri-prep-30 (Amicon, Beverly, Mass.) and then a Centricon-30 (Amicon) to reduce the volume to less than 200 ml. The concentrated supernatant is applied to a 2 ml phenylboronate (Pierce Chemical Company, Rockford, Ill.) column equilibrated with 100 mM Tris, pH 8.0. The column is washed with 2 mls of 100 mM Tris, pH 8.0. The effluent is then reapplied to the column to maximize the binding of the proteinase. The column is then washed with 5 bed volumes of 100 mM Tris, pH 8.0.

Purified proteolytic activity is eluted with 100 mM Tris, pH 8.0, 0.2M sorbitol and is recovered in the first bed volume of elution buffer. Fractions containing the proteinase are pooled and concentrated to less than 150 ml in a Centricon-30. The proteinase is precipitated with 9 volumes of −20° C. methanol, and then kept at −20° C. for 15 min. The precipitated proteinase is collected by centrifugation and resuspended in water. Protein concentrations are determined using the BCA assay from Pierce Chemical Company. The proteolytic activity is found to be associated with the intracellular extract, i.e., in association with cytoplasm as well as with cell membrane.

Cell Wall Extract exhibiting Proteolytic Activity. A cell wall extract is isolated as follows. 2.5 g of endophyte-infected *P. ampla* leaf sheath tissue is ground to a fine powder with liquid nitrogen and then homogenized in extraction buffer and centrifuged as above. The cell walls are washed 4 times with 10 mls of extraction buffer to remove residual intracellular proteinase At1. They are then extracted in 5 mls 100 mM Tris, pH 8.0, 1M NaCl.

As revealed in Tables I and II, the increasing levels of purification of the proteolytic activity in the steps forming the intracellular and cell wall extracts yield a extracts with increasing proteolytic activity:

TABLE 1

Formation of the Intracellular Extract

| Fraction | Total Protein (µg) | Total Activity[a] (units) | Specific Activity (units/µg protein × $10^{-3}$) | Purification |
|---|---|---|---|---|
| Crude Cytoplasmic Extract | 43,350 | 173 | 4 | 1 |
| First 100,000 × g Supernatant | 37,450 | 21 | 0.6 | — |
| First 100,000 × g Pellet | 5,851 | 161 | 27 | 7 |
| Second 100,000 × g Supernatant | 470 | 71 | 152 | 37 |
| Second 100,000 × g Pellet | 2,096 | 34 | 16 | — |
| Phenylboronate Column | 61 | 31 | 515 | 125 |
| Methanol Precipitated | 38 | 27 | 723 | 176 |

[a]Proteinase activity is quantified using 2% azoalbumin as the substrate. Sarath et al. Protease assay methods. In Proteolytic Enzymes, A Practical Approach by R. M. Beynon et al. IRL Press, Oxford, pp 25–55 (1989). The reaction buffer is 200 mM CAPS, pH 11.0, 20 mM DTT, and 1% SDS. Trichloroacetic acid soluble peptides are monitored spectrophotometrically at 440 nm. One unit is defined as a change of absorbance of one per hour.

TABLE II

Formation of the Cell Wall Extract

| Fraction | Protein (µg) | Total Activity[a] (units) | Specific Activity (units/µg protein × $10^{-3}$) |
|---|---|---|---|
| Cytoplasmic Extract | 42,780 | 287 | 6 |
| Wash 1 | 4,600 | 59 | 12 |
| Wash 2 | 1,450 | 38 | 26 |
| Wash 3 | 480 | 18 | 37 |
| Wash 4 | 330 | 13 | 39 |
| NaCl Extract | 476 | 288 | 606 |

TABLE II-continued

Formation of the Cell Wall Extract

| Fraction | Protein (μg) | Total Total Activity[a] (units) | Specific Activity (units/μg protein × $10^{-3}$) |
|---|---|---|---|
| of Cell Walls | | | |

[a]Proteinase activity is quantified using 2% azoalbumin as the substrate. Sarath et al. Protease assay methods. In Proteolytic Enzymes, A Practical Approach by R. M. Beynon et al. IRL Press, Oxford, pp 25-55 (1989). The reaction buffer is 200 mM CAPS, pH 11.0, 20 mM DTT, and 1% SDS. Trichloroacetic acid soluble peptides are monitored spectrophotometrically at 440 nm. One unit is defined as a change of absorbance of one per hour.

Proteolytic Activity of the Cell Wall and Intracellular Forms. In order to compare the proteolytic activity of the cell wall and intracellular extracts, endo-phyte-infected P. ampla leaf sheaths (0.4 g) are ground to a fine powder in liquid nitrogen and then homogenized in 1.6 mls 100 mM Tris, pH 8.0. The homogenate is centrifuged at 3,000 g for 10 min to pellet the cell walls. The cell wall pellet is washed twice with 30 mls 100 mM Tris, pH 8.0. The final cell wall pellet is resuspended in 1 ml 100 mM Tris, pH 8.0 and divided in half. Each sample is centrifuged at 3,000 g and the cell wall pellets extracted with either 400 ml 100 mM Tris, pH 8.0, 1M NaCl or with 400 ml 2×SDS sample buffer for 30 min. at room temperature. The samples are centrifuged 12,000 g and the supernatant fractions retained. The 1M NaCl extract is desalted through a Sephadex G-50 column. Aliquots (5 ml) of the cell wall extracts and the original cytoplasmic supernatant fraction are mixed with 5 ml 2×SDS sample buffer and electrophoresed on a SDS-gelatin activity gel. BSA degradation by the cell wall and cytoplasmic extracts is also assayed. Aliquots (55 ml) of the fractions are incubated with 100 mg of BSA in 2% SDS for 30 min at 24° C. Following the incubation the samples are boiled 5 min. and aliquots subjected to SDS-PAGE.

Figure 8A:
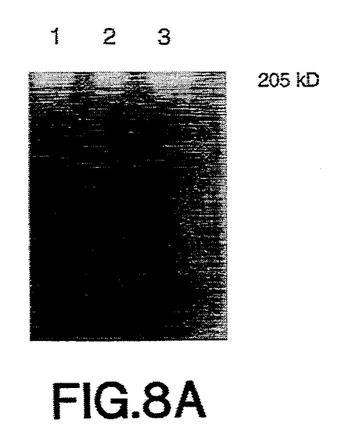
Figure 8B:
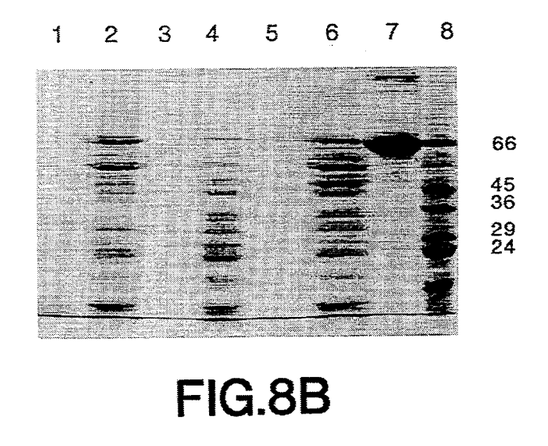

As seen in FIG. 8, the endoproteolytic activity is localized in both the intracellular and within cell wall extracts. Part A of FIG. 8 concerns SDS-gelatin activity gel of cytoplasmic and cell wall extracts of endophyte-infected P. ampla leaf sheath tissue: Lane 1, Cytoplasmic extract; lane 2, NaCl extract of the cell wall fraction; lane 3, SDS extract of the cell wall fraction. The 205,000 dalton marker is myosin. Part B concerns aliquots of the fractions described above incubated with 100 mg of BSA in 2% SDS for 30 minutes at 24° C., then subjected to SDS-PAGE: Lane 1, Cytoplasmic fraction; lane 2, cytoplasmic fraction incubated with BSA; lane 3, NaCl extract of the cell wall fraction; lane 4, NaCl extract of the cell wall fraction incubated with BSA; lane 5, SDS extract of the cell wall fraction; lane 6, SDS extract of the cell wall fraction incubated with BSA; lane 7, BSA control; lane 8, protein standards. The protein standards and their molecular weights are BSA, 66,000; egg albumin, 45,000; glyceraldehyde-3-phosphate dehydrogenase, 36,000; carbonic anhydrase, 29,000; trypsinogen, 24,000.

Figure 9A:
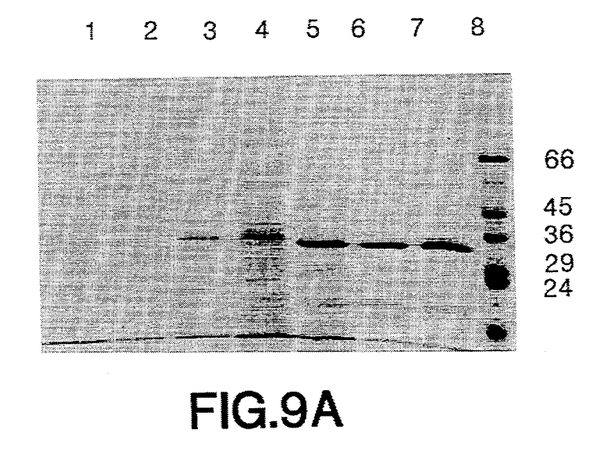
Figure 9B:
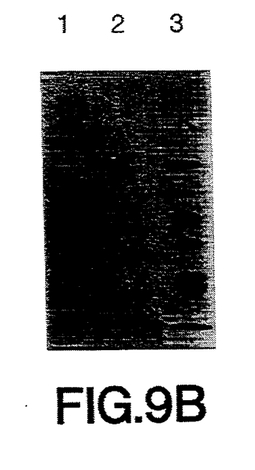

Electrophoretic Patterns of Proteolytic Activity of the Cell Wall and Intracellular Extracts. Purification of these extracts is performed as above. FIG. 9 presents SDS-PAGE analysis of the intracellular and cell walll-localized proteolytic activity. Part A of FIG. 9 concerns fractions from the purification of the intracellular proteolytic activity: Lane 1, Crude membrane fraction, 20 μg; lane 2, first 100,000 g supernatant, 20 μg; lane 3, first 100,000 g pellet, 20 μg; lane 4, second 100,000 g supernatant, 20 μg; lane 5, second 100,000 g pellet, 20 μg; lane 6, phenylboronate column eluate, 5 μg; lane 7, methanol precipitate 5 μg; lane 8, protein standards, as in FIG. 1. Part B concerns extraction of the cell wall activity: Lane 1, NaCl extract of the cell wall fraction, 2 μg; lane 2, purified intracellular proteinase, 2 μg; lane 3, protein standards as in FIG. 1.

Gel pattern of Bands having apparent molecular weight of 34,000 daltons. Following 5 minutes boiling of the intracellular and cell wall extracts, the major protein band has apparent molecular weight of 34,000 dalton (as seen in FIG. 9). Yet in SDS-gelatin activity gels, proteolytic activity migrates at an extremely high apparent molecular mass (as seen in FIG. 8A). The activity gels are obtained using unboiled enzyme whereas the fractions in FIG. 9 are boiled prior to electrophoresis.

These results indicate that the protein band having apparent molecular weight of 34,000 dalton band seen in the boiled samples is the denatured form of the active proteinase, which for some reason is not detected by staining. To confirm this relationship between the two bands, the intracellular extract is labeled with [1,3-$^3$H]DFP, an organophosphate serine protease inhibitor. DFP irreversibly binds to the catalytic serine of serine hydrolases. The labeled extract is divided into two aliquots, one of which is boiled prior to electrophoresis.

[1,3-$^3$H]diisopropylfluorophosphate (DFP) (111 GBq/mmol)is from NEN Research Products (Boston, Mass.). The labeling procedure is as described by Fagan and Waxman, Biochem Biophys Res Comm 178:856–861 (1991), incorporated herein by reference. Ten μg of intracellular extract, in 50 mM Tris, pH 8.0, 20 mM DTT, is incubated with 30 mM [1,3-$^3$H]DFP overnight at 4° C. As a control, the serine protease chymotrypsin is also labeled. The samples are then mixed with an equal volume of 2×SDS sample buffer (Laemmli, 1970). One half of each sample is boiled for 5 min. SDS-PAGE is then carried out on the unboiled and boiled aliquots. Identical, unlabeled samples are also electrophoresed on the same gel. Following electrophoresis, the gel is cut in half and the portion with the unlabeled samples is stained with coomassie brilliant blue. The portion of the gel containing the radiolabeled samples is treated with EN$^3$HANCE (NEN Research Products) and subjected to fluorography.

Figure 10:
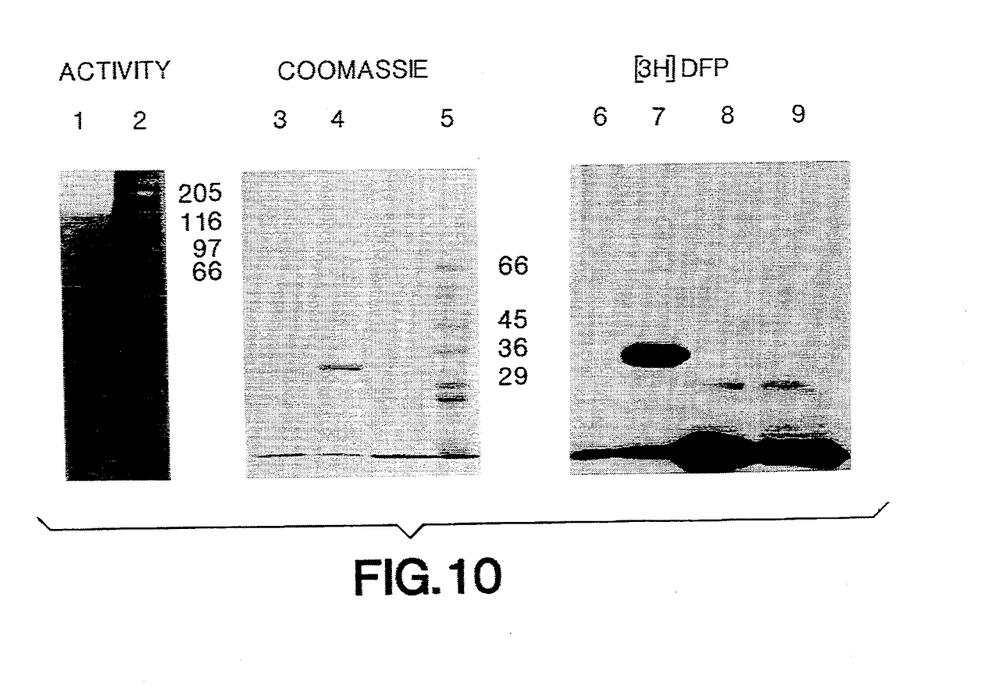

The results of FIG. 10 are as follows: Lane 1, SDS-gelatin activity gel of 500 ng. of unboiled purified intracellular proteinase At1; lane 2, high molecular weight protein standards which are myosin (205,000), β-galactosidase (116,000), phosphorylase b (97,400), and BSA (66,000); lane 3, coomassie stained SDS gel of 2 μg of unboiled purified proteinase At1; lane 4, 2 μg of boiled purified proteinase At1; lane 5, low molecular weight protein standards as in FIG. 1; lane 6, autoradiogram of 10 μg of [$^3$H]DFP-labeled unboiled purified proteinase At1; lane 7, 10 μg of [$^3$H]DFP-labeled boiled purified proteinase At1; lane 8, 10 μg of [$^3$H]DFP-labeled unboiled chymotrypsin; lane 9, 10 μg of $^3$H]DFP-labeled boiled chymotrypsin. The radioactivity in the unboiled sample is a smear in the region of the gel corresponding to the position of protease activity (FIG. 10, lanes 1 and 6). There is also a small amount of radioactivity which barely enters the stacking gel and is detectable in the well.

The coomassie staining of the active form reflects what is seen with the [$^3$H]DFP-labeling. There is some staining in the well (data not shown) and a faint smear throughout the lane (FIG. 10, lane 3). After boiling, the radioactivity is converted to a sharp band of 34,000 dalton (FIG. 10, lane 7). The position of [$^3$H]DFP-labeled chymotrypsin is the same in both the unboiled and boiled samples (FIG. 10, lanes 8 and 9). Binding of [$^3$H]DFP to the proteinase in the intracellular extract confirms that the denatured proteinase migrates as a 34,000 dalton protein.

Presence of a Thiol Group. In order to test whether a thiol group is present in the proteinase of the intracellular extract, fluorescein-5-maleimide (F5M) or 5-iodoacetamidofluorescein (IAF) (both from Pierce Chemical Company) is mixed into the intracellular extract. (Five $\mu$l of 500 mM IAF or 5 ml of 120 mM F5M are added.) The protein is dissolved in 20 mM KCl, 50 mM imidazole, pH 7.5, 1% SDS, boiled 3 minutes and then DTT is added to 10 mM. All samples are held overnight on ice followed by 2 hours at room temperature. The pH is maintained at 7.5 by adding 0.5 $\mu$l of 10M NaOH. Samples are kept at room temperature in the dark for two hours. An equal volume of 2×SDS loading buffer is added and the proteins fractionated by SDS gel electrophoresis. Gels are rinsed with water and proteins visualized by excitation at 312 nm on a UV transilluminator.

The results appear in FIG. 11: Lane 1, intracellular extract combined with 5-iodoacetamidofluorescein; lane 2, intracellular extract combined with fluorescein-5-malemide. The position of the proteinase is indicated by the arrow. The proteinase of the intracellular extract contains at least one thiol group.

Presence of Carbohydrate Groups. The unusual electrophoretic behavior of the proteolytic activity, along with its localization to both an intracellular and a cell wall extract, indicate it may contain carbohydrate groups. The presence or absence of glycoprotein in the proteinase is ascertained by the binding of biotinylated lectins to the purified intracellular proteinase. Lectins used are *Pisum sativum* agglutinin, wheat germ agglutinin and peanut agglutinin (all from Pierce Chemical Company). The presence of the proteinase is indicated in this assay using an immunodiagnostic tool.

Figure 14:
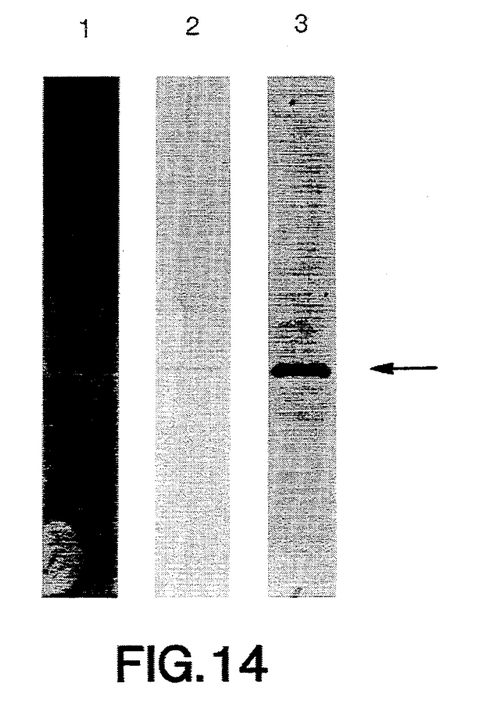

The results of this test are as seen in FIG. 14. Proteinase At1 is a glycoprotein: Lane 1, *Pisum sativum* agglutinin; lane 2, wheat germ agglutinin; lane 3, peanut agglutinin. The position of the 34,000 dalton proteinase At1 band is indicated by the arrow. Lectins binding the 34,000 dalton proteinase band are: *Pisum sativum* agglutinin which binds $\alpha$-linked mannose and $\alpha$-linked glucose, wheat germ agglutinin which binds N-acetylglucosamine, and peanut agglutinin which binds galactosyl end-groups.

Effect of pH and Temperature. The effects of pH and temperature on the proteolytic activity of the intracellular extract are measured in duplicate. One assay employs 2% azo-albumin as the substrate, in 200 mM cyclohexylamino-1-propane sulfonic acid (CAPS), pH 11, 20 mM DTT, 1% SDS. After a two hour incubation at 24° C., trichloroacetic acid, soluble peptides are monitored spectrophotometrically at 440 nm. The effect of pH on proteinase activity is also quantified using the tetrapeptide substrate succinyl-Ala-Ala-Pro-Phe-4-nitroanilide (Boehringer Mannheim, Indianapolis, Ind.).

For the determination of the effect of pH on activity, SDS is not included in the assay buffer. The following buffers are used: pH 6 and 7, bis-(2-hydroxyethyl)iminotris(hydroxymethyl)methane (Bis-Tris); pH 7, 8 and 9, 1,3-bis[tris(hydroxymethyl)-methylamino]propane (Bis-Tris propane); pH 9 and 10,3-(cyclohexylamino)-2-hydroxy-1-propanesulfonic acid, sodium salt (CAPSO); pH 10 and 11, CAPS. For each pH, duplicate samples containing 1 $\mu$g of purified proteinase are assayed. The change in absorbance at 400 nm is monitored in a Beckman DU-64 spectrophotometer (Beckman Instruments, Palo Alto, Calif.). The results are expressed as pmoles of product produced sec-1.

Figure 12A:
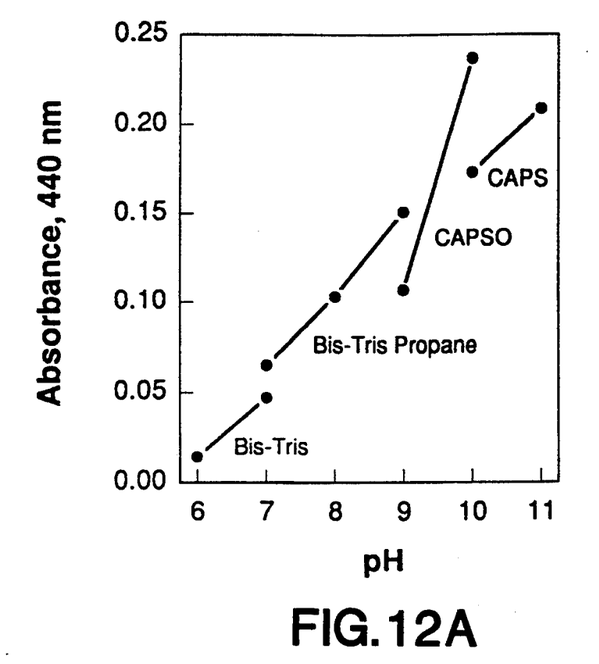
Figure 12B:
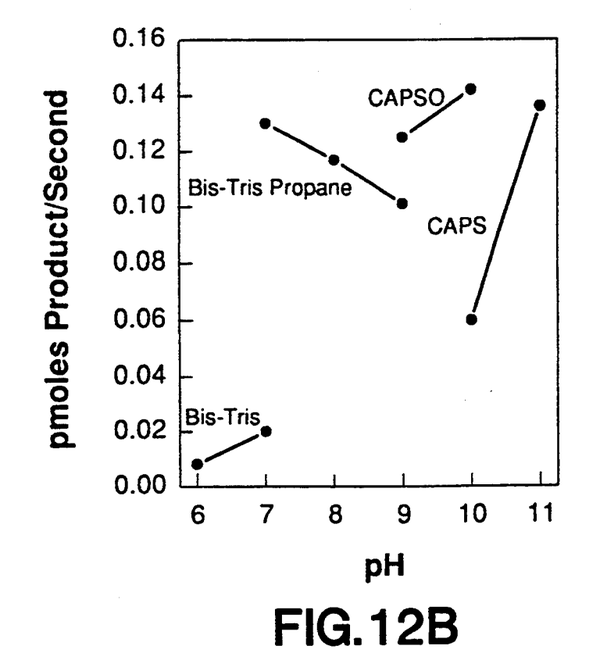

FIG. 12 illustrates the effect of pH on the proteolytic activity. Each point is the mean of duplicate samples. Part A concerns activity using azoalbumin as the substrate. Part B concerns activity using succinyl-Ala-Ala-Pro-Phe-4-nitroanilide as the substrate.

With azoalbumin as the substrate, the activity is highest at pH 10-11 (FIG. 12A). With the tetrapeptide as the substrate, similar levels of activity are observed over the pH range 7-11, although there are differences in activity dependent on the buffer used (FIG. 12B). The sharp response to pH seen with azoalbumin as the substrate may reflect the effect of pH on azoalbumin itself, and the generation of a more accessible substrate, rather than an effect on the enzyme. With both substrates, the pH range of activity indicates that proteinase At1 is an alkaline proteinase.

In assays measuring the effect of temperature variation, azoalbumin digestion by 3 $\mu$g of purified proteinase is quantified in 200 mM CAPS, pH 11.0, 20 mM DTT. Duplicate samples are incubated for two hours at 27°, 37°, 42°, 55° and 65° C. Additionally, one $\mu$g of proteinaceous material from the intracellular extract in 2×SDS sample buffer, is incubated at these temperatures for two hours and then subjected to SDS-PAGE, without prior boiling. A control aliquot is boiled for 5 min. prior to electrophoresis.

Figure 13:
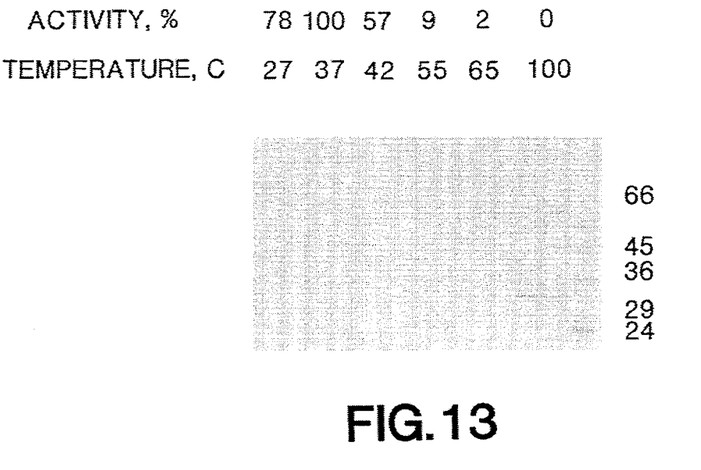

As seen in FIG. 13, the proteolytic activity is seen to be best between 27° C. and 42° C., with a maximum at 37° C. At 55° C., the activity is less than 10% of that at 37° C. Temperature increases may affect the conformation of the proteinase. Disruption of the active form, and appearance of the 34,000 dalton band, occurs with increasing temperature, concomitant with the decrease in protease activity. A faint band is detectable (at 34,000 dalton)in the sample incubated at 55° C., with increasing amounts detectable at 65° C. and in the boiled sample.

Regulation of At1 Expression. High levels of the endoproteolytic activity are detected in extracts of primary cultures of the fungus, i.e. those established directly from surface-sterilized leaf sheath tissue. On subsequent subculture of the fungus, this activity is either not detectable or is detectable at low levels, indicating that expression of the responsible proteinase is regulated by the fungus.

Extracts of fungal tissue 3, 5, 7, and 14 days following transfer from PDA to MS plus sucrose are prepared by homogenization in 2×SDS sample buffer. Aliquots are subjected to SDS-PAGE and immunoblot analysis is performed using the affinity purified antiserum.

Figure 15:
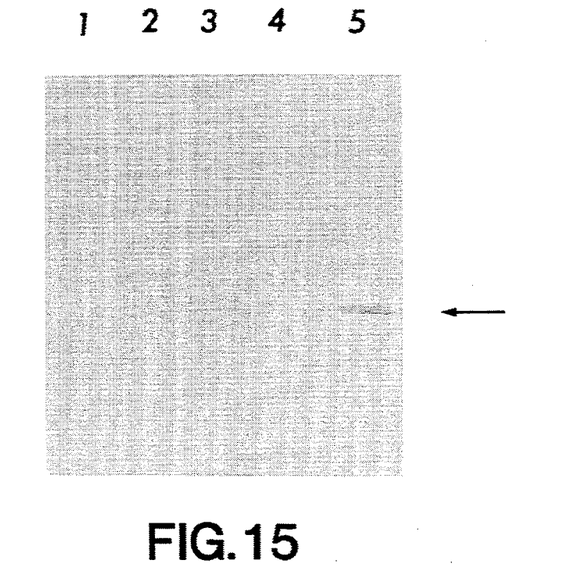

The results are seen in FIG. 15: Lane 1, 3 days following subculture; Lane 2, 5 days following subculture; Lane 3, 7 days following subculture; Lane 4, 14 days following subculture; Lane 5, 0.5 micrograms of purified proteinase At1. From immunoblot analysis, expression of the proteinase is not detectable in cultures 3 or 5 days following subculture from PDA to MS plus sucrose but is detectable 7 and 14 days following subculture.

C. PROTEINASE At1

The proteolytic activity present in the crude membrane fraction, the intracellular and cell wall extracts described above is due to proteinase At1. Proteinase At1 is derivable from the crude membrane fraction, the intracellular and the cell wall extracts described above. It is reactive with BCA and exhibits optimal endo-proteolytic activity at 35°–40° C. and at pH 10–11; however, the endo-proteolytic activity is exhibited only when a reductant is present. The protease inhibitor PMSF does inhibit this activity, but protease inhibitors EDTA, EGTA, phenanthroline, E-64 and DCl do not. Neither the presence of detergent nor by methanol precipitation inhibit the activity of proteinase At1.

Proteinase At1 has a first gel electrophoresis band with apparent molecular weight of 205,000 daltons when electrophoresed without prior boiling. If boiled prior to electrophoresis, the proteinase is seen instead to produce a band having apparent molecular weight of 34,000 daltons. This 34,000 dalton band comprises a thiol group, reacts with biotinylated lectins selected from the group consisting of *P. sativum* agglutinin, wheat germ agglutinin, and peanut agglutinin, and gives rise to polyclonal rabbit antibodies which do not cross react with proteinase K.

Without in any way limiting the invention, Applicants wish to express their understanding that the above laboratory results regarding this proteinase indicate that it is very likely a thiol-containing serine protease which is a glycoprotein, bearing carbohydrate groups including α-linked mannose, α-linked glucose, N-acetyl glucosamine, and galactosyl end-groups, D. A SIMILAR PROTEINASE FROM OTHER Poa SPECIES In order to determine if the fungal protease is unique to *A. typhinum* infecting *P. ampla*, the proteolytic activity of leaf sheath extracts from other endophyte-infected grasses to degrade BSA in 2×SDS buffer is measured.

Figure 7:
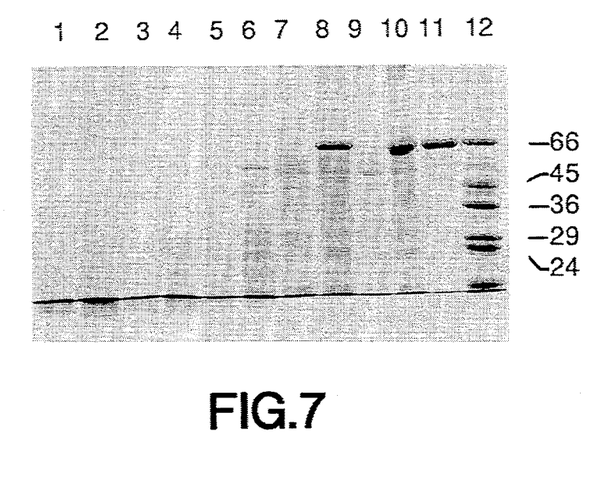

Extracts from endophyte-infected *P. ampla*, *P. autumnalis* and *P. sylvestris* are found to degrade BSA (as seen in FIG. 7, lanes 2, 4 ,and 6). Protease activity during the 1 h incubation also results in extensive degradation of proteins in the tissue extracts (FIG. 7, lanes 1, 3, and 5). Similar protease activity is detected in extracts of the Acremonium endophytes isolated from these plants.

Extracts from *F. arundinacea* and *L. perenne* did not degrade BSA (FIG. 7, lanes 8 and 10), and the protein profile of the extracts alone did not appear degraded (FIG. 7, lanes 7 and 9). *F. arundinacea* is infected with *A. coenophialum*, and *L. perenne* is infected with *A. Iolii*.

Proteinase activity similar to proteinase At1 is also detected in two other endophyte-infected Poa spp., *P. autumnalis* Muhl. ex Ell. and *P. sylvestris* A. Gray, but not in endophyte infected *L. perenne* or *F. arundinacea* (Lindstrom et al., *Plant Physiol.* 102, 645–650, 1993). Immunoblot analysis of crude leaf sheath extracts of the above and 3 additional endophyte-infected Poa sp., *P. arctica* R. Br., *P. interior* Rydb., and *P. palustris* L. is performed as follows. Leaf sheath crude membrane fractions are prepared by homogenization in 2×SDS sample buffer. Aliquots are subjected to immunoblot analysis using the proteinase At1 antiserum, and SDS-gelatin activity gel analysis.

Polyclonal rabbit antibodies are prepared against the 34,000 dalton band. Boiled, purified proteinase At1 (100 mg) from the intracellular extract is fractionated by SDS-PAGE. The gel is stained with cold 0.25M KCl, 1 mM DTT (Hager and Burgess, 1980) and the 34,000 dalton band excised. The gel slice is finely minced in 500 ml of phosphate buffered saline (200 mM NaCl, 9 mM phosphate, pH 7.2). The homogenized gel is injected into the subscapular space of a white New Zealand rabbit (Weintraub and Raymond, 1963). Three injections of about 100 mg of protein are given at 4 week intervals. Serum is collected and antibody specific to the proteinase is prepared through affinity purification on nitrocellulose. The proteinase antigen is briefly boiled in 0.02% SDS then bound to nitrocellulose at 11 mg antigen per square centimeter. Nitrocellulose strips are washed 3 times in TBS (20 mM Tris, pH 7.5, 180 mM NaCl), then blocked in 3% BSA in TBS for 1 hour. Strips are incubated overnight in a 1:5 dilution of serum in 3% BSA in TBS.

After incubation, the nitrocellulose strips are washed for 1 hour with four changes in TBS. Purified rabbit antibodies are eluted in 5 mM glycine-HCl, pH 2.3, 500 mM NaCl, 100 mg/ml BSA. Strips are sequentially placed in 5 microfuge tubes containing 750 ml of elution buffer. The strip is placed into elution buffer, agitated for thirty seconds then transferred to the next tube. Each tube is neutralized with 75 ml of 0.5M Na2HPO4. The tubes containing eluted antibody are pooled and concentrated to 1 ml in a Centricon-10 (Amicon).

Gels for immunoblots are transferred to Immobilon-P (Millipore, Marlborough, Mass.) in 10 mM CAPS, pH 11, 10% methanol. Membranes are blocked in BLOTTO (5% non-fat dry milk in TBS) for 1 hour, then incubated overnight in a 1:2000 dilution of the antibody in TTBS (0.05% Tween-20 in TBS). Membranes are washed four times in TTBS for 15 minutes each wash then incubated in a 1:3000 dilution of goat anti rabbit IgG alkaline phosphatase conjugate (Bio-Rad, Hercules, Calif.) for one hour. Membranes are washed three times in TTBS prior to color development using BCIP/NBT (as described in Sambrook et al., *Molecular Cloning, A Laboratory Manual*, 2nd Ed., Cold Spring Harbor Laboratory Press, Cold Spring Harbor, N.Y. 1989 incorporated herein by reference). Blots using affinity purified antibody are incubated overnight in a 1:50 dilution of the purified antibody then processed as above.

Proteinase At1 (1.5 mg) from the intracellular extract is fractionated by SDS-PAGE and transferred to Immobilon-P. Membranes are blocked in TBS, 3% BSA and then incubated in a 1 mg/ml solution of biotinylated lectin in TBS, 0.3% BSA, 0.05% Tween-20 (wash buffer).

Blots are rinsed in wash buffer 3 times at ten minutes per wash. Proteins are visualized using a streptavidin-alkaline phosphatase complex (Oxford Glycosystems, Rosedale, N.Y.) followed by color development with BCIP/NBT.

Figure 16A:
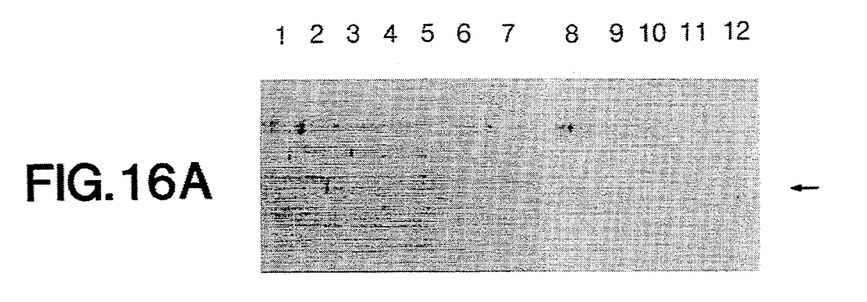
Figure 16B:
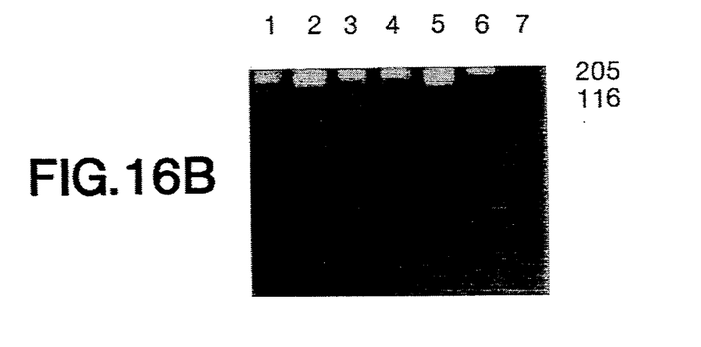

As seen in the FIG. 16, Part A immunoblot analysis using proteinase At1 antiserum. FIG. 16 presents the results of an antigenically similar proteinase being expressed in other endophyte-infected Poa spp: Lane 1, Endophyte-infected *P. ampla;* lane 2, endophyte-infected *P. arcfica;* lane 3, endophyte-infected *P. autumnalis;* lane 4, endophyte-infected *P. interior;* lane 5, endophyte-infected *P. palustris;* lane 6, endophyte-infected *P. sylvestris;* lane 7, 1 μg of purified intracellular proteinase At1; lane 8, endophyte-free *P. ampla;* lane 9, endophyte-infected *F. arundinacea;* lane 10, endophyte-infected *L. perenne;* lane 11, 1 μg of purified intracellular proteinase At1; lane 12, 1 μg cell wall proteinase At1 (NaCl extract of endophyte-infected *P. ampla* leaf sheath cell wall fraction). B. SDS-gelatin activity gel. Lanes 1-6 are the same as lanes 1-6 in A; lane 7, high molecular weight protein standards as in FIG. 3.

The proteinase At1 antiserum does recognize the 34,000 dalton band of these other species (FIG. 16A, lanes 1-6). The tissues are homogenized in 2×SDS buffer which would solubilize both intracellular and cell wall proteinase activity, both of which are recognized by the antibody (FIG. 16A, lanes 11 and 12). Additionally, in SDS-gelatin activity gels, proteinase activity, with similar electrophoretic migration as that of proteinase At1, is detected in all the above endophyte-infected Poa spp. (FIG. 16B). No cross reacting material (FIG. 16A, lanes 8, 9 and 10) or proteinase At1-like activity (FIG. 7) is detected in endophyte-free *P. ampla* or in endophyte-infected *L. perenne* or *F. arundinacea*.

E. DETERGENT COMPOSITION

In a further embodiment, there is provided a composition comprising one of the proteinases described above and one or more detergents. Suitably the proteinase may be proteinase At1. Alternatively, the proteinase in the composition may be one of the proteinases isolated from one of the strain of grasses selected from the group consisting of *P. arctica* R. Br., *P. autumnalis* Muhl. ex Ell., *P. interior* Rydb., *P. palustris* L., and *P. sylvestris* A. Gray, described above.

The amount of proteinase in the detergent composition may be that used in conventional compositions known to those skilled in the art, i.e., from about 0.01% to 5.0% by weight. Similarly, the amount of one or more detergents may be that used in conventional compositions known to those skilled in the art, i.e., from about 0.5 to about 25% by weight, or from 1% to 15% by weight, or from 2 to 10% by weight. Suitable detergents include conventional anionic, nonionic and cationic detergents well known to those skilled in the art. The detergent composition may be made according to steps well known to those skilled in the art.

Such a detergent composition may be used in cleaning soiled surfaces or objects. In particular, the composition may be used to expose the surface or object to endoproteolytic activity, thus cleaving proteinaceous material on or associated with said surface or object, to facilitate removal therefrom. Alternatively, the detergent composition would be useful in analyzing biological materials. Such materials usually include proteinaceous matter; subjecting the unpurified material to analytical procedures, e.g., SDS gel electrophoresis, in the presence of this detergent composition will result in the material's proteins being digested. Consequently, analysis and purification of the remaining contents of the material will be facilitated.

E. BIOLOGICALLY PURE CULTURE

A further embodiment of the invention is a biologically pure culture of the microorganism *A. typhinum* having the identifying characteristics of ATCC 74228. This culture is capable of producing the detergent-resistant proteinase in recoverable amounts. Biologically pure cultures are not believed to be produced in nature, since this fungus grows as an endophyte in grasses.

A biologically pure culture of *A. typhinum* deposited on Jun. 9, 1993 with the American Type Culture Collection (ATCC), 12301 Parklawn Drive, Rockville, Md. 20852, USA, under the provision of the Budapest Treaty for the International Recognition of the Deposit of Microorganisms for the Purposes of Patent Procedure and Title 37 Section 1.801 et seq. of the Code of Federal Regulations, was accorded ATCC Accession No. 74228 ("*A. typhinum* ATCC 74228"). This culture produces proteinase At1.

It is noted that the deposited material is not considered to be essential to the practice of the claimed invention and that the grant of admission to the depository to distribute samples of the biological material does not constitute an express or implied license to practice the invention claimed in any patent issuing from the instant application or from any continuation, divisional or reissue application thereof.

The primary identifying characteristics of the biologically pure culture of the microorganism *A. typhinum* are described in Morgan-Jones and Gams, *Mycotaxon*, XV, 311-318 (July-September 1982), incorporated herein by reference. One further characteristic is that the culture is capable of producing the proteinase At1 in recoverable amounts.

Purification of the microorganism *A. typhinum* having the identifying characteristics of ATCC 74228 may be carried out in the isolation of mycelial extracts from the grass described above. A variant of this embodiment is a biologically pure culture of *A. typhinum* ATCC 74228 which produces recoverable amounts of the proteinase of claim 1. This biologically pure culture may be isolated using the steps for isolating the above pure culture.

F. PROCESS OF SYNTHESIZING PROTEINASE At1

In another embodiment, there is provided a process of synthesizing the proteinase At1 comprising cultivating a biologically pure culture of *A. typhinum* ATCC 74228 under conditions suitable for the formation of said proteinase and recovering the proteinase in substantially pure form. The biologically pure culture is isolated and maintained as described above. Conditions suitable for the formation of the proteinase include growing said biologically pure culture in an in vitro cell culture, or introducing said biologically pure culture into an endophyte-free grass, suitably a grass selected from the group consisting of grasses in the Poa species. The recovery of the proteinase in substantially pure form may be performed using those techniques described above for isolating the intracellular or cell wall extracts of proteinase At1. In light of the high volume of proteinase At1 synthesized intracellularly in an endophytic *A. typhinum*, one suitable process of synthesizing proteinase At1 is by introducing a biologically pure culture of *A. typhinum* ATCC 74228 as an endophytic infection into a grass of the Poa spp., for example *P. ampla* and forming an intra cellular extract of said grass. This process further provides the proteinase At1 made by the above steps.

The invention now being fully described, it will be apparent to one of ordinary skill in the art that many changes and modifications may be made thereto without departing from the spirit or scope of the invention as set forth herein.

We claim:

1. A crude membrane fraction of *Acremonium typhinum* ATCC 74228 exhibiting endoproteolytic activity, said activity:

being reactive with bicinchoninic acid;

being optimal at 35°–40° C. and at pH 10–11;

being exhibited only when a reductant is present;

being inhibited by the protease inhibitor phenylmethylsulfonyl fluoride, but not by protease inhibitors ethylenediamine tetraacetic acid, ethylenebis(oxyethylenenitrilo)tetraacetic acid, phenanthroline, L-transepoxysuccinyl-leucylamido(4-guanidino)butane and 3,4-dichloroisocumarin, by the presence of detergent, or by methanol precipitation;

being associated with a first gel electrophoresis band having apparent molecular weight of 205,000 daltons when said extract is electrophoresed without prior boiling, said extract, when boiled prior to electrophoresis, instead producing a band having apparent molecular weight of 34,000 daltons;

said 34,000 dalton band comprising a thiol group, reacting with biotinylated lectins selected from the group consisting of *Pisum safivum* agglutinin, wheat germ agglutinin, and peanut agglutinin, and giving rise to polyclonal rabbit antibodies which do not cross react with proteinase K.

2. A cell wall extract of *Acremonium typhinum* ATCC 74228, said extract being reactive with bicinchoninic acid and exhibiting the endoproteolytic activity of claim 1.

3. An intracellular extract of *Acremonium typhinum* ATCC 74228, said extract being reactive with bicinchoninic acid and exhibiting the endoproteolytic activity of claim 1.

4. The intracellular extract of claim 3 isolated from leaf sheath tissue of a grass endophytically infected by *Acremonium typhinum* ATCC 74228.

5. The intracellular extract of claim 4 wherein said grass is selected from the group consisting of *Poa ampla, Poa arctica, Poa autumnalis, Poa interior, Poa palustris,* and *Poa sylvestris.*

6. The intracellular extract of claim 5 wherein said grass is *Poa ampla.*

7. The intracellular extract of claim 5 derived from a culture of said *Acremonium typhinum* selected from the group consisting of a primary culture established directly from surface-sterilized leaf tissue of said grass endophytically infected by *Acremonium typhinum* ATCC 74228 and a sub-culture of said primary culture established 7–14 days after said primary culture has been established.

8. A proteinase which is derived from said intracellular extract of claim 3, said proteinase being reactive with bicinchoninic acid and exhibiting endoproteolytic activity, said activity:

being optimal at 35°–40° C. and at pH 10–11;
being exhibited only when a reductant is present;
being inhibited by the protease inhibitor phenylmethylsulfonyl fluoride, but not by protease inhibitors ethylenediamine tetraacetic acid, ethylenebis(oxyethylenenitrilo)tetraacetic acid, phenanthroline, L-transepoxysuccinyl-leucylamido(4-guanidino)butane and 3,4-dichloroisocouomarin, by the presence of detergent, or by methanol precipitation;

being associated with a first gel electrophoresis band having apparent molecular weight of 205,000 daltons when said proteinase is electrophoresed without prior boiling, said proteinase, when boiled prior to electrophoresis, instead producing a band having apparent molecular weight of 34,000 daltons;

said 34,000 dalton band comprising a thiol group, reacting with biotinylated lectins selected from the group consisting of *Pisum sativum* agglutinin, wheat germ agglutinin, and peanut agglutinin, and giving rise to polyclonal rabbit antibodies which do not cross react with proteinase K.

9. A proteinase isolated from a crude membrane fraction of an *Acremonium typhinum* ATCC 74228 endophytically infected grass selected from the group consisting of *Poa arctica* R. Br., *Poa autumnalis* Muhl ex Ell., *Poa interior* Rydb., *Poa palustris* L., and *Poa sylvestris* A. Gray, said proteinase being reactive with bicinchoninic acid and exhibiting endoproteolytic activity;

said activity:
being exhibited only when a reductant is present;
being uninhibited by the presence of detergent or by methanol precipitation;
being associated with a first gel electrophoresis band having apparent molecular weight of 205,000 daltons when said proteinase is electrophoresed without prior boiling, said proteinase, when boiled prior to electrophoresis, instead producing a band having apparent molecular weight of 34,000 daltons;
said 34,000 dalton band being immunologically cross-reactive with the polyclonal rabbit antibodies specific to the proteinase of claim 8.

10. A composition comprising a substantially pure proteinase of claim 8 and one or more detergents.

11. A biologically pure culture of *Acrmonium typhinum* ATCC 74228 which produces recoverable amounts of the proteinase of claim 8.

12. A process of synthesizing the proteinase of claim 8 comprising cultivating a biologically pure culture of *Acremonium typhinum* ATCC 74228 under conditions suitable for the formation of said proteinase and recovering said proteinase in substantially pure form.

* * * * *